United States Patent [19]

Murtha et al.

[11] 4,177,166

[45] Dec. 4, 1979

[54] HYDROALKYLATION COMPOSITION AND PROCESS FOR PRODUCING SAID COMPOSITION

[75] Inventors: Timothy P. Murtha; Ernest A. Zuech, both of Bartlesville, Okla.

[73] Assignee: Phillips Petroleum Company, Bartlesville, Okla.

[21] Appl. No.: 865,159

[22] Filed: Dec. 28, 1977

Related U.S. Application Data

[62] Division of Ser. No. 739,152, Nov. 5, 1976, Pat. No. 4,118,434.

[51] Int. Cl.$^2$ .............................................. B01J 29/06
[52] U.S. Cl. ................................................. 252/455 Z
[58] Field of Search ...................................... 252/455 Z

[56] References Cited

U.S. PATENT DOCUMENTS

| 3,173,854 | 3/1965 | Eastwood et al. | 252/455 Z |
| 3,706,694 | 12/1972 | Young | 252/455 Z |
| 3,783,123 | 1/1974 | Young | 252/455 Z |
| 3,963,788 | 6/1976 | Kruse et al. | 252/455 Z |
| 3,966,643 | 6/1976 | Scherzer et al. | 252/455 Z |

*Primary Examiner*—Carl Dees

[57] ABSTRACT

An aromatic hydrocarbon is contacted under hydroalkylation conditions and in the presence of hydrogen with a composition comprising at least one ruthenium compound impregnated on a calcined, acidic, nickel and rare earth-treated crystalline zeolite support.

11 Claims, No Drawings

HYDROALKYLATION COMPOSITION AND PROCESS FOR PRODUCING SAID COMPOSITION

This is a division of application Ser. No. 739,152, filed Nov. 5, 1976, U.S. Pat. No. 4,118,434.

The invention relates to a hydroalkylation process, a composition useful as a catalyst in said process and a method for producing said composition.

Prior art catalysts in the field of hydroalkylation processes suffered from several drawbacks. These deficiencies of the prior art catalysts for the hydroalkylation reaction included: (1) Many prior art compositions useful as catalysts show a rather low productivity as judged by the low liquid hourly space velocities (LHSV) that are utilized in the prior art. Thus a more active and more selective hydroalkylation catalyst is desired. (2) A number of the catalysts of the prior art for the hydroalkylation reaction are prepared by very complex and time consuming processes. For example, starting with a powdered crystalline zeolite support, said support is cation exchanged, washed and then incorporated into a matrix of another material such as silica-alumina. This combination is calcined, cooled, and impregnated with certain metal salts. Finally the composite is extruded into pellets and the like. Thus it is desirable that a more simplified and less expensive process for making active and selective catalysts be found. (3) Certain catalysts of the prior art for the hydroalkylation reaction were of fixed acidity because of the type of support material utilized. This left little variation that could be made in this important property of the hydroalkylation catalyst. It is therefore desirable that catalysts be developed which are varied easily in their acidity characteristics.

It is an object of the present invention to hydroalkylate aromatic compounds.

Another object of the present invention is to provide a method for producing a composition useful as a hydroalkylation catalyst.

Another object of the invention is a composition useful as a catalyst in hydroalkylation reactions which is more active and more selective than prior art catalysts.

Another object of the invention is a composition useful as a catalyst in hydroalkylation reactions which is simpler and less expensive to produce as compared to prior art catalysts.

Still another object of the invention is a composition useful as a catalyst in hydroalkylation reactions in which the acidity of the catalyst can be adjusted.

SUMMARY

According to the invention an aromatic hydrocarbon is contacted under hydroalkylation conditions and in the presence of hydrogen with a composition comprising a calcined, acidic, nickel and rare earth-treated crystalline zeolite support impregnated with at least one ruthenium compound subsequent to calcination. Such a composition is useful as a catalyst which is a highly active and selective catalyst.

Further according to the invention a composition comprises a calcined acidic nickel and rare earth-treated crystalline zeolite support impregnated with at least one ruthenium compound subsequent to calcination.

Further according to the invention the above composition is prepared by contacting a crystalline zeolite with an aqueous cation exchange solution comprising rare earth, nickel and ammonium compounds; removing the zeolite from said solution and washing said zeolite with water to remove excess ions; calcining said zeolite; cooling said calcined zeolite; impregnating said calcined zeolite with a solution comprising at least one ruthenium compound in a suitable solvent; and removing said solvent by evaporation. This process allows the acidity of the composition to be easily adjusted by varying the conditions under which the cation exchange step is carried out.

DETAILED DESCRIPTION OF THE INVENTION

The composition of the instant invention can be briefly described as a crystalline zeolite which has been cation exchanged with rare earth, nickel and ammonium compounds followed by a calcination step and said calcined support then impregnated with at least one ruthenium compound to give the final composition. Although not absolutely necessary, it is preferred that the above catalyst be treated with hydrogen prior to introduction of the aromatic hydrocarbon feed in the hydroalkylation process because of improved results.

The compositions of the instant invention are useful as catalysts and to some extent solve or obviate each of the above-mentioned deficiencies of the prior art catalysts. For example, they appear to operate at higher levels of productivity in that they show a higher degree of activity and selectivity than certain of the prior art catalysts; the process of making the compositions of the instant invention is simple and straight-forward and the compositions thus obtained should be less expensive than those of the prior art which utilize very complex steps in their preparation; and the compositions of the instant invention can be made with a high degree of flexibility in the degree of acidity simply by adjusting the cation exchange conditions on the crystalline zeolite support utilized for the compositions of this invention.

The support material for the composition employed in the instant invention is a crystalline zeolite which has been treated under cation exchange conditions with a mixture of rare earth, nickel and ammonium compounds such that the cationic metal content of the support is partially exchanged. Generally the cationic metal is an alkali metal which is removed by cation exchange such that the residual alkali metal content ranges from about 0.01 to about 2 percent by weight; however, the runs carried out in accordance with the invention and reported herein indicate that good results can be obtained employing an alkali metal content ranging from about 0.1 to about 1 percent by weight. The more commonly employed crystalline zeolites which are suitable for use in accordance with the present invention are the Type X or Type Y crystalline zeolites which are sometimes called molecular sieves because of their essentially uniform pore diameters. Some suitable Type Y synthetic crystalline zeolites are described for example in U.S. Pat. No. 3,130,007 and some suitable Type X zeolites are described in U.S. Pat. No. 2,882,244. Such materials are presently commercially available as for example zeolites SK-40 (Type Y) and 13X (Type X) from the Linde Division of Union Carbide Corporation, New York, N.Y.

The alkali metal form of the crystalline zeolites usually comprises sodium as the alkali metal and said zeolites are treated under cation exchange conditions with a mixture of rare earth, nickel and ammonium compounds in accordance with the present invention in order to provide a suitable support material for use in the preparation of the compositions of the invention.

It is contemplated that any of the readily available rare earth metal compounds can be employed. Generally, the compounds used are those in which the rare earth metal-containing ion is present in the cationic state. Representative rare earth metal compounds include nitrates, bromides, acetates, chlorides, iodides, sulfates and mixtures thereof of one or more of the rare earth metals including cerium, lanthanum, praseodymium, neodymium, samarium, europium, gadolinium, terbium, dysprosium, holmium, erbium, thulium, ytterbium, and lutetium. Compounds of the rare earths named above may be employed singly, however, it is often convenient to employ mixtures of the rare earths as these are commercially available. For example, mixtures of rare earth metal compounds such as the chlorides of lanthanum, cerium, praseodymium, neodymium, samarium and gadolinium are available commercially at a relatively low cost and may be effectively employed.

As noted above, the zeolite material is cation exchanged with a mixture of rare earth, nickel and ammonium compounds according to the instant invention. Any convenient ammonium compound may be employed although the chloride is preferred because it is inexpensive and readily available. The weight ratio of ammonium compound to nickel and rare earth compounds in the aqueous exchange solution can be selected over a broad range. Generally the weight ratio of ammonium compound to nickel and rare earth compounds is within the range of from about 0.05:1 to about 20:1, although the data contained herein indicates that a range of from about 0.2:1 to about 5:1 can be used with good results. The concentration of rare earth compounds in the aqueous exchange solution can be varied over a wide range and exchange conditions can be adjusted accordingly such that the rare earth content of the ion exchanged crystalline zeolite can be adjusted over a broad range. Generally, the content of the final catalyst composite in terms of the rare earth elements is from about 2 to about 25 weight percent. The runs described herein indicate that the rare earth content of the catalyst can be within the range of from 5 to 20 weight percent. Good results were obtained employing a rare earth content of about 10 percent by weight. As noted above, the alkali metal content, for example sodium, of the exchanged catalyst support is generally from about 0.01 to about 2 percent by weight; however, the runs described herein indicate that good results can be obtained employing an alkali metal content ranging from about 0.1 to about 1 percent by weight.

The nickel compounds which will be employed in admixture with the above-named rare earth metal compounds and ammonium compounds are those wherein the nickel ion is present in the cationic state. Some suitable compounds representative of the nickel compounds which can be used in the invention include the nitrates, bromides, acetates, chlorides, iodides, sulfates and mixtures thereof.

The nickel content in the final composition can also be selected over a broad range. Generally the composition will comprise from about 0.01 to about 15 weight percent nickel, although the runs carried out in accordance with the invention and described herein indicate that good results can be obtained employing a nickel content ranging from about 1 to about 8 percent by weight.

The procedure whereby the Type X and Type Y zeolites are treated with aqueous solutions of rare earth, nickel and ammonium compounds to replace a portion of the alkali metal content of the zeolite is a cation exchange process which can be carried out in a batch or continuous fashion. Generally the exchange process is carried out on a continuous basis under the following typical conditions. A fixed bed of the zeolite material is treated with said aqueous solution of the rare earth, nickel and ammonium compounds at a temperature of 90° to 110° C. under conditions such that from about 0.1 to about 0.5 of the volume of aqueous salts solution per volume of zeolite is in contact with said zeolite per hour or, in other words, an LHSV ranging from about 0.1 to about 0.5 is employed in the exchange process. Under these conditions, the exchange process can be completed in 48 hours or less to achieve the desired level of rare earth, nickel and ammonium ions in the zeolite. The exchanged zeolite is then washed free of excess ions from the exchange step with water. The excess wash water is removed by drying the zeolite at a temperature ranging from about 100°–300° C. and thereafter slowly increasing the temperature within the range of from about 200° to about 550° C. in order to calcine the zeolite and convert the ammonium cations to the hydrogen form. Usually, the calcination is conducted until a constant weight is obtained for the zeolitic material, generally from about 2 to about 10 hours. The calcined zeolite is then cooled in ambient air, i.e., under conditions of normal humidity. The zeolite support thus prepared is now ready for impregnation with ruthenium in order to prepare the compositions of the instant invention.

The above described support is then impregnated with a solution of at least one ruthenium compound followed by evaporation of the solvent used in the impregnation step. Evaporation of the solvent can be conducted under vacuum if desired. Some suitable solvents include water, alcohols, such as ethanol, ketones, such as acetone, and the like. Some of the various ruthenium compounds which can be employed in the impregnation step, are the ruthenium compounds such as the nitrates, acetates, and mixtures thereof. Particularly preferred are the chlorides because of availability and ease of handling. The impregnation is generally carried out under what may be called "total impregnation" whereby the entire solids in the solutions used in the impregnation are left on the catalyst support and the liquid solvent for said compounds is simply removed by evaporation.

The ruthenium content in the final composition can be selected over a broad range. Generally the ruthenium content ranges from 0.01 to about 1 percent by weight although the runs described herein indicate that good results can be obtained employing a ruthenium content within the range of from about 0.05 to 0.25 percent by weight.

The composition described above is employed for the hydroalkylation of aromatic hydrocarbons to produce cycloalkyl aromatic hydrocarbons. The feedstocks which are suitable for use in the present invention are aromatic compounds, such as for example, monocyclic aromatic hydrocarbons and alkylsubstituted monocyclic aromatic hydrocarbons. Some specific examples of these are benzene, toluene, xylenes, and mixtures thereof. The aromatic hydrocarbon feedstocks should be essentially free of sulfur-containing compounds and other known poisons for hydrogenation catalysts in general. However, it is believed that a small amount of water, e.g., 10–20 ppm, in the feedstock is beneficial for maintaining catalyst activity over an extended period, e.g., several days.

The invention is particularly valuable for the conversion of benzene to cyclohexylbenzene. Cyclohexylbenzene is known as a valuable solvent and chemical intermediate. It can be converted in high yield to phenol and cyclohexanone by autooxidation with subsequent acid treatment. It is also useful as an intermediate in the production of cyclohexene which in turn can be utilized for the production of adipic acid and caprolactam.

The aromatic hydrocarbon feedstock is fed to the catalyst in a reaction zone operated under a wide range of conditions. The feedstock liquid hourly space velocity (LHSV), reaction temperature and pressure, and the hydrogen feed rate are not particularly critical; however, the liquid hourly space velocity (LHSV) generally ranges from about 1 to about 100, the reaction pressure generally ranges from about 690 to about 13,800 kPa (about 100 to about 2,000 psig), the hydrogen feed rate generally ranging from about 0.2 to about 1 mole per mole of aromatic hydrocarbon feedstock per hour, and the reaction temperature generally ranging from about 100° to about 250° C. Based upon the runs described herein good results can be obtained employing a liquid hourly space velocity (LHSV) within the range of from about 5 to about 25, a reaction pressure within the range of from about 1,380 to about 6,900 kPa (about 200 to about 1,000 psig), the hydrogen feed rate within the range of from about 0.2 to about 1 mole per mole of aromatic hydrocarbon feed per hour, and the reaction temperature within the range of from about 140° to about 200° C.

The hydroalkylation reaction is conveniently carried out by having the above described composition used as a catalyst in a fixed bed reactor and then contacting said composition with the aromatic hydrocarbon feed and hydrogen in an upflow or downflow arrangement. It is also possible to employ a countercurrent flow of hydrogen and the aromatic hydrocarbon feed over the catalyst in the reaction zone. It is also possible to carry out the hydroalkylation reaction under batch conditions although a batch process is less preferred, because it is normally more expensive to operate and initial equipment costs are higher based upon the same size process.

Although a fixed bed reactor is mentioned above, most any type of reaction zone can be used as the particular type of reaction zone is not believed to be a critical parameter of the invention.

The reaction mixture from the reaction zone can usually be conveniently separated into the desired components by simple fractional distillation, and recycle of the unreacted feedstock and unreacted hydrogen can be accomplished as desired. The hydroalkylation products can be further purified as desired after separation from unreacted feedstock.

It generally is desirable to pretreat the catalyst with hydrogen gas prior to contacting the catalyst with the aromatic hydrocarbon in order to prereduce the catalyst. Based upon the runs described hereinafter, the hydrogen pressure and feed rate for the pretreating step generally is the same as that to be employed when contacting the aromatic hydrocarbon with the catalyst. In the hydroalkylation runs of the examples hereinafter described, the catalyst in the reactor was first reduced at 150° C. for 15 minutes under 3,450 kPa (500 psig) hydrogen at a hydrogen flow rate of 0.32 liters per minute before benzene was introduced to the reactor. Hydrogen pressure during the hydroalkylation process was maintained at 3,450 kPa (500 psig) and at a flow rate of about 0.32 liters per minute.

EXAMPLE I

A glass tube of 45 millimeter diameter which was equipped with heating means and means for passing an aqueous solution of compounds therethrough was charged with 200 grams of a Type X crystalline zeolite (Davison Chemical Division of W. R. Grace and Co., Baltimore, MD, 10 A mole sieves). The crystalline zeolite was in the form of spherical particles of about ⅛" diameter. An aqueous solution of 200 grams of ammonium chloride, 100 grams of rare earth chlorides, and 40 grams of nickel chloride hexahydrate in 4 liters of deionized water was prepared. Said rare earth chlorides were utilized as a commercially available mixture from the American Potash Corporation of the following composition:

$MCl_3 \cdot 6H_2O$ wherein M=Lanthanum 23%, cerium 43.5%, praseodymium 5.4%, neodymium 17.9%, samarium 1.9%, gadolinium 0.6%, and others 0.2%. The above-described aqueous solution was then pumped over the bed of crystalline zeolite particles at an LHSV of about 0.25. The temperature of the cation exchange zone was kept at about 95° to 105° C. After the solution had been pumped through the crystalline zeolite bed, the material was cooled, filtered and then washed six times with 350 ml portions of water. The cation exchanged zeolite material was then allowed to dry for about three hours. The cation exchanged crystalline zeolite was then calcined by slowly heating in a furnace up to 288° C. (550° F.) over a six-hour period. The material was kept at this temperature for 2 hours and then heated slowly to 594° C. (1100° F.) for about three hours and finally cooled back to 288° C. (550° F.) and maintained at this temperature for about 24 hours. The crystalline zeolite was allowed to dry in ambient air and there was recovered 195.2 grams of the calcined zeolite. The above-mentioned cation exchanged zeolite contained 12.49% rare earths, 0.98% sodium, and 2.1% nickel by analysis. No ruthenium was present in the catalyst (No. 1) thus prepared. The catalyst, 15 ml (10.0 g), was prereduced with hydrogen at 400° C. for about three hours under 3,450 kPa (500 psig) hydrogen at a hydrogen flow rate of 0.32 liters per minute. Said catalyst was utilized in benzene hydroalkylation runs at temperatures ranging from 210° up to 430° C. and at liquid hourly space velocities ranging from about 10 to about 20 but only trace conversion of benzene feed was indicated under these conditions. The results of these runs demonstrate that a catalyst without ruthenium shows low activity under the conditions utilized in the hydroalkylation of benzene to cyclohexylbenzene.

EXAMPLE II

Other runs were made in the preparation of catalysts within the scope of the instant invention by utilizing the catalyst material described in Example I above as the support material. Thus, the nickel, rare earth metal, and sodium content of the final catalysts are expected to be essentially the same as that shown for catalyst (No. 1) of Example I. Catalyst (No. 2) was prepared by taking 30 grams of the calcined support material of the above-described catalyst No. 1 and then impregnating this amount of the material with a solution of 0.0747 grams of ruthenium trichloride in about 80 ml of absolute ethanol. The ethanol was removed under reduced pressure on a rotary evaporator followed by the addition of more ethanol and the evaporation step repeated. Catalyst No. 3 in this example was a physical mixture of 7.5 ml of catalyst No. 2 and 7.5 ml of catalyst No. 1 from Example I. Catalyst No. 4 of this example was prepared by treating 30 grams of the calcined support material of catalyst No. 1 with a solution of 0.0372 gram of ruthenium trichloride in about 80 ml of absolute ethanol. The ethanol was removed under reduced pressure on a rotary evaporator. About 20 ml of additional ethanol was then added to the catalyst material and evaporated again as described above. The above-described catalysts (Nos. 2, 3, and 4) were employed in benzene hydroalkylation runs for the preparation of cyclohexylbenzene. The conditions employed in said runs and the results obtained are presented below in Table I. Gas-liquid phase chromatography (GLC) was utilized in the analysis of the reaction mixture effluent from the reaction zone.

Each catalyst was prereduced at 150° C. for 15 minutes under 3,450 kPa (500 psig) hydrogen at a hydrogen flow rate of 0.32 liters per minute. The hydroalkylation runs were conducted under the same hydrogen pressure and flow rate as that used in the prereduction step.

LHSV at a temperature of about 90° to 100° C. The zeolite material was allowed to cool then filtered and washed six times with 350 ml portions of water and then allowed to dry in the air. The material was next heated overnight at 140° C. and then the temperature gradually increased over about nine hours from 160° C. to 517° C. The material was then allowed to cool in ambient air. The final weight was 162.8 grams. Analysis indicated a sodium content of 0.22 weight percent and a nickel content of 2.5 weight percent. The catalyst support thus prepared by cation exchange of a Type X crystalline zeolite with a mixture of ammonium chloride and rare earth chlorides followed by exchange with nickel chloride was impregnated with ruthenium chloride in order to prepare an active hydroalkylation catalyst. Thirty grams of the above-described support material was impregnated with a solution of 0.0375 grams of ruthenium trichloride in about 80 ml of ethanol. The ethanol was removed under reduced pressure in a rotary evaporator. The final catalyst contained 0.05 weight percent ruthenium, 2.5 weight percent nickel and about 14 weight percent rare earth metals. This catalyst, No. 5, was utilized in benzene hydroalkylation runs under the conditions shown below in Table II and the results of Table I

| Run No. | Catalyst No. | Wt. Amount, ml(g) | % Ru[a] | Temp. °C. | LHSV | Benzene Conv. % | Selectivity, % CHB[b] | Ratio CHB/CH[c] |
|---|---|---|---|---|---|---|---|---|
| 1 | 2 | 15(13) | 0.10 | 154 | 20 | 10.1 | 62 | 2.3 |
| 2 | 3 | 15(11.6) | 0.05 | 151 | 33 | 8.7 | 58 | 1.9 |
| 3 | 3 | " | 0.05 | 173 | 40 | 11.3 | 65 | 2.9 |
| 4 | 4 | 15(13.3) | 0.05 | 162 | 22 | 11.3 | 74 | 5.2 |
| 5 | 4 | " | 0.05 | 150 | 24 | 11.2 | 77 | 5.4 |
| 6 | 4 | " | 0.05 | 145 | 24 | 11.3 | 79 | 6.9 |

[a]Based on total catalyst employed.
[b]CHB = cyclohexylbenzene
[c]CH = cyclohexane The results of Table I show that the catalysts of the instant invention provide high selectivity to cyclohexylbenzene in a benzene hydroalkylation process and at reasonably good benzene conversion rates.

EXAMPLE III

Another catalyst of the instant invention was prepared in which the cation exchange step of a Type X crystalline zeolite with the ammonium and rare earth compounds was first carried out followed by subsequent cation exchange with a nickel compound. Two hundred grams of the Type X crystalline zeolite utilized as the starting material in Example I was wet with a solution of 400 grams of ammonium chloride and 200 grams of the mixed rare earth chlorides of Example I in 4 liters of water. The dampened crystalline zeolite was charged to the cation exchange reactor utilized in Example I, and the solution described above pumped over the crystalline zeolite at about 0.25 LHSV at a temperature of about 95°–100° C. The material was filtered and washed six times with 350 ml portions of water and allowed to dry in the air. The crystalline zeolite was then heated for about four hours at about 168° C. (335° F.) after which the temperature was increased gradually to 538° C. (1000° F.) over about three hours. The material was removed from the furnace while still hot and allowed to cool in ambient air. The above material which had been cation exchanged with the mixture of ammonium and rare earth compounds was then recharged to the exchange reactor and a solution of 200 grams of nickel chloride hexahydrate in 4 liters of water was pumped over the crystalline zeolite at about 0.25 the hydroalkylation runs are also shown therein. The catalyst was prereduced as in Example II and utilized under the same hydrogen pressure and flow rate as that described in Example II.

TABLE II

| Run No. | Catalyst Amount, ml(g) | Temp. °C. | LHSV | Benzene Conv., % | Selectivity, % CHB | Ratio CHB/CH |
|---|---|---|---|---|---|---|
| 8 | 15(14) | 205 | 6.7 | 9.1 | 64 | 4.1 |
| 9 | " | 180 | 6.7 | 4.7 | 76 | 7.4 |

The results in Table II demonstrate the suitability of catalyst No. 5 for the hydroalkylation of benzene to cyclohexylbenzene.

EXAMPLE IV

Another catalyst was prepared according to the instant invention. 200 grams of the same crystalline zeolite utilized in Example I was wetted with a solution of 400 grams of ammonium chloride, 200 grams of the mixed rare earth chlorides of Example I, and 100 grams of nickel chloride hexahydrate in 4 liters of distilled water. The wetted crystalline zeolite was charged to the cation exchange reactor utilized in Example I and the above-described solution pumped over the zeolite at about 0.25 LHSV at a temperature of about 95° C. The mixture was cooled, filtered and the zeolite washed six times with 350 ml portions of water and then allowed to air dry. The cation exchanged zeolite was then calcined in generally the same manner as that utilized for the catalyst of Example I (No. 1). The recovered material weighed 167.2 grams and by analysis showed a sodium content of 0.6 weight percent, a nickel content of 2.6 weight percent. The rare earth metal content was about 14 weight percent. Thirty grams of the above prepared support was impregnated with 0.0370 grams of ruthenium trichloride in about 80 ml of absolute ethanol. The ethanol was removed under reduced pressure in a rotary evaporator. Ruthenium content of the catalyst was 0.05 weight percent. The catalyst described above (No. 6) was utilized in benzene hydroalkylation runs to produce cyclohexylbenzene. The catalyst was prereduced as in Example II and utilized under the same hydrogen pressure and flow rate as in Example II. The results of these runs are shown below in Table III.

TABLE III

| Run No. | Catalyst No. | Amount, ml(g) | Temp. °C. | LHSV | Benzene Conv. % | Selectivity % CHB | Ratio CHB/CH |
|---|---|---|---|---|---|---|---|
| 10 | 6 | 15(12.7) | 150 | 11.8 | 7.4 | 77 | 5.4 |
| 11 | 6 | " | 175 | 12.5 | 11.8 | 80 | 10.1 |

The results in Table III illustrate again the good selectivity to cyclohexylbenzene at reasonably good benzene conversion which can be achieved utilizing a catalyst of the instant invention for the hydroalkylation of benzene.

EXAMPLE V

Another catalyst (No. 7) was prepared to examine the effect of calcining the final catalyst composite after impregnation of the support material with the ruthenium trichloride. In this run, a solution of 400 grams of ammonium chloride, 100 grams of the mixed rare earth chlorides of Example I and 200 grams of nickel chloride hexahydrate in 4 liters of water was prepared. Two hundred grams of the same crystalline zeolite utilized as a starting material in Example I was wetted with the above solution and then charged to the cation exchange reactor. The remaining solution was pumped over the crystalline zeolite at about 0.25 LHSV at a temperature of about 90°-100° C. The material was cooled and washed six times with 350 ml portions of water and allowed to dry in the air. One-half of the above cation exchanged zeolite (113.8 grams) was then calcined in the usual manner to give a product which weighed 83.5 grams. Analysis of this product indicated 4.68% nickel, 9.5% rare earth metals and 0.63% sodium by weight. However, 27.3 grams of the uncalcined zeolite material was impregnated with 0.054 grams of ruthenium trichloride in 25 ml of water and the water evaporated. This material was then heated at 93°-149° C. (200°-300° F.) for about 20 hours and then the temperature slowly increased over about 8 hours to 524° C. (975° F.) and the material then removed from the furnace. This catalyst material weighed 20.1 grams and contained 0.10 weight percent ruthenium. Catalyst No. 7 prepared as described above in which the catalyst was calcined after ruthenium impregnation was employed in benzene hydroalkylation runs to produce cyclohexylbenzene with the results obtained shown below in Table IV. The catalyst was prereduced as in Example II and utilized under the same hydrogen pressure and flow rate as in Example II.

Table IV

| Run No. | Catalyst No. | Amount, ml(g) | Temp. °C. | LHSV | Benzene Conv. % | Selectivity % CHB | Ratio CHB/CH |
|---|---|---|---|---|---|---|---|
| 12 | 7 | 13.5(10) | 170 | 9.6 | 8.5 | 21 | 0.3 |
| 13 | 7 | " | 210 | 9.6 | 8.1 | 44 | 0.9 |

The results of Table IV indicate a drastic decrease in selectivity for cyclohexylbenzene when the catalyst was calcined after the ruthenium was added to the zeolite support by impregnation.

EXAMPLE VI

As a further demonstration of the advantage of preparing the catalyst of the instant invention in the particular method described, another catalyst was prepared by charging 200 grams of the crystalline zeolite Type X employed in Example I to the cation exchange reactor. The crystalline zeolite was cation exchanged with a solution of 400 grams of ammonium chloride and 200 grams of the mixed rare earth chlorides utilized in Example I. The temperature employed in the cation exchange step was from about 95°-105° C. at a liquid hour space velocity of about 0.25. The reaction mixture was cooled and filtered and the zeolite material washed six times with 350 ml portions of water. After the zeolite was dried in air it was then placed in a furnace and calcined in the same manner as that described for Example I above. The cation exchanged crystalline zeolite which had been calcined weighed 195.6 grams. The sodium content of this calcined support material was 0.65 percent by weight and the rare earth content was 16.37 percent by weight. Thirty grams of the cation exchanged and calcined Type X zeolite was then impregnated with a solution of 0.0745 grams of ruthenium trichloride and 0.1217 grams of nickel chloride in about 80 ml of absolute ethanol. The ethanol was removed under reduced pressure on a rotary evaporator. More ethanol was added and then removed as before. This step was repeated before the catalyst was recovered for use. This catalyst (No. 8) contained 0.10 weight percent ruthenium and 0.10 weight percent nickel. The above-described catalyst (15 ml, 12.7 g) was utilized in a series of benzene hydroalkylation runs, including one run in which the benzene conversion level and temperature employed were approximately the same as those shown for Run 6 utilizing catalyst number 4 of Table I above. Catalyst No. 8 was prereduced as in Example II and utilized under the same conditions of hydrogen pressure and flow rate as in Example II. For the purposes of comparison, the results of the run using catalyst No. 8, Run 14, is shown in Table V below along with the results from Run 6 using catalyst number 4 of Table I of this invention.

Table V

| Run No. | Catalyst No. | Temp. °C. | LHSV | Benzene Conv. % | Selectivity % CHB | Ratio CHB/CH |
|---|---|---|---|---|---|---|
| 14 | 8 | 150 | 15 | 13.7 | 78 | 6.5 |
| 6[a] | 4 | 145 | 24 | 11.3 | 79 | 6.9 |

[a] Catalyst volume was 15 ml and catalyst weight 13.3 g.

Based on the results shown in Table V above the productivity of catalyst No. 8 can be compared with that of catalyst No. 4 of the instant invention. Calculations show that the productivity of catalyst No. 8, a catalyst outside the scope of the invention, in terms of grams of cyclohexylbenzene produced per gram of ruthenium per hour is 1897 while the productivity in terms of the same units for catalyst No. 4 in Run No. 6 of the instant invention is 4872. Thus, the catalyst of the instant invention was about 2.5 times more productive as compared to a similar catalyst outside the scope of this invention.

What is claimed is:

1. A composition consisting essentially of:
    a calcined, acidic nickel and rare earth-treated crystalline zeolite support impregnated with at least one ruthenium compound subsequent to calcination wherein the ruthenium content is within the range of about 0.01 to about 1 percent by weight of the composition.

2. The composition of claim 1 wherein the ruthenium content ranges from about 0.05 to about 0.25 percent by weight.

3. The composition of claim 1 wherein the crystalline zeolite is selected from the group consisting of Type X and Type Y zeolites;
    wherein the rare earth and nickel compounds are selected from the group consisting of nitrates, bromides, acetates, chlorides, iodides, sulfates and mixtures thereof;
    wherein the rare earth metal is selected from the group consisting of cerium, lanthanum, praseodymium, neodymium, samarium, europium, gadolinium, terbium, dysprosium, holmium, erbium, thulium, ytterbium, lutetium and mixtures thereof, and
    wherein the ruthenium compounds are selected from the group consisting of nitrates, acetates and mixtures thereof.

4. The composition of claim 1 wherein the crystalline zeolite is the alkali metal form with the alkali metal content of the calcined, acidic, nickel and rare earth-treated crystalline zeolite ranges from about 0.01 to about 2 percent by weight;
    wherein the rare earth content of the calcined, acidic, nickel and rare earth-treated crystalline zeolite ranges from about 2 to about 25 percent by weight; and
    wherein the nickel content of the calcined, acidic, nickel and rare earth-treated crystalline zeolite ranges from about 0.01 to about 15 percent by weight.

5. The composition of claim 1 wherein the crystalline zeolite is the alkali metal form with the alkali metal content of the calcined, acidic, nickel and rare earth-treated crystalline zeolite ranges from about 0.05 to about 1 percent by weight;
    wherein the rare earth content of the calcined, acidic, nickel and rare earth-treated crystalline zeolite ranges from about 5 to about 20 percent by weight; and
    wherein the nickel content of the calcined, acidic, nickel and rare earth-treated crystalline zeolite ranges from about 1 to about 8 percent by weight.

6. The composition of claim 1 wherein the crystalline zeolite is selected from the group consisting of Type X and Type Y zeolites; and
    the ruthenium compound is ruthenium trichloride, the nickel compound is nickel chloride hexahydrate, and the rare earth metal compound used to treat the crystalline zeolite is a mixture of the chlorides of at least lanthanum, cerium, praseodymium, neodymium, samarium and gadolinium.

7. A method for the preparation of a composition comprising:
    contacting a crystalline zeolite with an aqueous cation exchange solution comprising rare earth, nickel, and ammonium compounds;
    removing the zeolite from said solution and washing said zeolite with water to remove excess ions;
    calcining said zeolite;
    cooling said calcined zeolite;
    impregnating said calcined zeolite with a solution comprising at least one ruthenium compound in a suitable solvent wherein the ruthenium content of the impregnating solution is sufficient to provide a ruthenium content of the cation exchange zeolite within a range of from about 0.01 to about 1 percent by weight zeolite; and
    removing said solvent by evaporation.

8. The method of claim 7 wherein said zeolite is selected from the group consisting of alkali metal Type X and Type Y zeolites;
    wherein the rare earth and nickel compounds are selected from the group consisting of nitrates, bromides, acetates, chlorides, iodides, sulfates and mixtures thereof;
    wherein the rare earth metal is selected from the group consisting of cerium, lanthanum, praseodymium, neodymium, samarium, europium, gadolinium, terbium, dysprosium, holmium, erbium, thulium, ytterbium, lutetium and mixtures thereof; and
    wherein the ruthenium compounds are selected from the group consisting of nitrates, acetates and mixtures thereof;
    the weight ratio of ammonium compound to rare earth and nickel compounds ranges from about 0.05:1 to about 20:1;
    said aqueous cation exchange rare earth, nickel and ammonium compound solution is contacted with said zeolite at a liquid hourly space velocity ranging from about 0.1 to about 0.5;
    after said zeolite is washed with water and prior to said calcination step, said zeolite is heated to a temperature ranging from about 100° to about 300° C. to remove excess water and then the temperature is slowly raised to a temperature ranging from about 200° to about 550° C. in order to calcine said zeolite and convert the ammonium cations to the hydrogen form.

9. The method of claim 7 wherein said composition is treated with hydrogen subsequent to the removal by evaporation of said ruthenium compound solvent.

10. The method of claim 7 wherein said zeolite is selected from the group consisting of alkali metal Type X and Type Y zeolites;
    wherein the rare earth and nickel compounds are selected from the group consisting of nitrates, bromides, acetates, chlorides, iodides, sulfates and mixtures thereof;
    wherein the rare earth metal is selected from the group consisting of cerium, lanthanum, praseodymium, neodymium, samarium, europium, gadolinium, terbium, dysprosium, holmium, erbium, thulium, ytterbium, lutetium and mixtures thereof, and wherein the ruthenium compounds are selected from the group consisting of nitrates, acetates and mixtures thereof;

the weight ratio of ammonium compound to rare earth and nickel compounds ranges from about 0.05:1 to about 20:1;

said aqueous cation exchange rare earth, nickel and ammonium compound solution is contacted with said zeolite at a liquid hourly space velocity ranging from about 0.05 to about 0.25;

after said zeolite is washed with water and prior to said calcination step, said zeolite is heated to a temperature ranging from about 100° to about 300° C. to remove excess water and then the temperature is slowly raised to a temperature ranging from about 200° to about 550° C. in order to calcine said zeolite and convert the ammonium cations to the hydrogen form.

11. The method of claim 7 wherein the crystalline zeolite is selected from the group consisting of Type X and Type Y zeolites; and the ruthenium compound is ruthenium trichloride, the nickel compound is nickel chloride hexahydrate, and the rare earth metal compound used to treat the crystalline zeolite is a mixture of the chlorides of at least lanthanum, cerium, praseodymium, neodymium, samarium and gadolinium.

* * * * *